United States Patent [19]

Behnam et al.

[11] Patent Number: 4,900,520

[45] Date of Patent: Feb. 13, 1990

[54] PROCESS FOR REMOVAL OF SOLUBLE PLATINUM GROUP METAL CATALYSTS FROM LIQUID PRODUCT MIXTURES

[75] Inventors: Basil A. Behnam, Mississauga; Rastko Vukov, Toronto, both of Canada

[73] Assignee: GAF Chemicals Corporation, Wayne, N.J.

[21] Appl. No.: 265,167

[22] Filed: Oct. 31, 1988

[51] Int. Cl.[4] .................... C01G 55/00; C22B 11/00
[52] U.S. Cl. .................... 423/22; 75/101 BE; 75/0.5 B; 75/83; 75/121; 502/12; 210/688; 549/215; 556/479; 556/419; 556/415; 556/437; 556/445; 556/450
[58] Field of Search .............. 556/479, 419, 415, 437, 556/445, 450, 457; 549/215; 423/22; 210/688; 502/12; 75/101 BE, 0.5 B, 83, 121

[56] References Cited

U.S. PATENT DOCUMENTS

| | | | |
|---|---|---|---|
| 2,371,119 | 3/1945 | Nachod | 423/22 |
| 2,726,141 | 12/1955 | Appell | 423/22 |
| 3,001,868 | 9/1961 | Avèston | 423/22 |

FOREIGN PATENT DOCUMENTS 0151435  9/1983  Japan .

Primary Examiner—Patrick P. Garvin
Assistant Examiner—E. D. Irzinski
Attorney, Agent, or Firm—Marilyn J. Maue; Joshua J. Ward

[57] ABSTRACT

A process for the neutralization, clarification and decolorization of organosilanes or organosilicones derived from the reaction of an organosilane or a hydropolysiloxane with an aliphatically unsaturated compound in the presence of an acidic platinum catalyst, a process for the conversion of a soluble platinum catalyst into an insoluble form and a process for the recovery of a platinum catalyst from an insoluble anion exchange resin which comprises:

(a) contacting a reaction mixture of the organosilane or organosilicone with a basic anionic exchange resin having a free amino or quaternized ammonium salt functionality in an insoluble polymeric matrix under conditions suitable to bind the soluble platinum catalyst to said resin;

(b) separating said resin containing bound platinum catalyst from the organosilane or organosilicone reaction mixture and, optionally, (c) treating the separated resin with an inorganic base to convert the bound platinum catalyst to a recoverable salt or (d) subjecting the resin containing bound platinum catalyst to combustion to recover elemental platinum.

17 Claims, No Drawings

PROCESS FOR REMOVAL OF SOLUBLE PLATINUM GROUP METAL CATALYSTS FROM LIQUID PRODUCT MIXTURES

BACKGROUND OF THE INVENTION

The syntheses of organosilanes and organosilicone polymers are well known and generally involve catalytic hydrosilylation of an aliphatically unsaturated compound with a silane or a silicon polymer containing reactive silanic-hydrogen,

and/or hydrogen-siloxy,

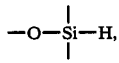

units in the presence of small amounts of acidic platinum catalyst, e.g. chloroplatinic acid. While relatively high conversions to organosilanes and organosiloxanes are achieved, the crude product is unsuitable for many applications since it has a hazy appearance or amber coloration which is caused by entrainment of extremely low levels (ppm), of residual platinum catalyst. Such products are particularly unsuitable for cosmetic and personnel use applications. More importantly, because of the high cost of platinum catalysts, it is economically judicious to recover even small residual amounts from the crude product mixture and preferably to recover the platinum in a purity suitable for reuse. In prior operations, where product is recovered by neutralization and filtration, these small amounts of platinum are generally unrecoverable from the filter cake.

One method which has been proposed for removal of platinum involves the neutralization of the reaction product with an excess of metal bicarbonate and the use of pressure filters to remove the resulting salt. Although this method accomplishes some lightening of the highly colored product, it is inefficient and fails to provide a truly clear, colorless product.

Several other methods have been proposed for removal of platinum catalyst to reduce haze and coloration of the organosilane/organosilicone product. Such methods include the treatments involving tedious and time consuming extractions with liquids, filtrations or contact of the reaction mixture with clays, magnesium silicate or magnesium sulfate decolorization agents or filtering aids. However, the high concentration of inorganic clarifying agents needed to achieve a reasonably clear product, prevent recovery of platinum by economical methods. Accordingly, these traces of platinum catalyst entrained in the inorganic clarifier are lost in the process.

Still another method, such as that disclosed in U.S. Pat. No. 3,745,206, involves contacting the reaction mixture from which platinum catalyst is to be removed with a solid carrier having a thiol or thioether functional silicone bonded to its surface and subsequent washing with aqua regia to dissolve and separate entrained platinum from the solid carrier. Since the removal of platinum catalyst from the reaction mixture depends on entrainment in the solid carrier, relatively large amounts of this silicone surface carrier must be used and consequently significant amounts of aqua regia are required to recover the platinum from the carrier. Also, the recovery of platinum by this method requires special corrosion resistant equipment and involves handling and disposal of hazardous corrosive concentrated acids which renders the entire process environmentally objectionable and economically unfeasible for commercial use.

Accordingly, it is an object of this invention to overcome the disadvantages described above and to provide a clear, substantially colorless organosilane or organosiloxane product.

Another object of this invention is to provide a simplified, more efficient process which employs inexpensive chemicals of low toxicity.

Another object of this invention is to provide a process for the recovery of trace amounts of a platinum group metal catalyst form an organosilane or organosiloxane synthesis mixture and from the organosilicone products or from other synthesis mixtures and products.

Another object is to recover the platinum group metal catalyst in the form of elemental metal and in a high yield and purity suitable for reuse in catalytic or other reactions.

Another object is to recover platinum in the form of a platinum salt or as chloroplatinic acid in high yield and purity.

Still another object of the invention is to provide simultaneous neutralization of a hydrosilylation reaction mixture while removing color and haze from the organosilane and organosiloxane product.

Another object is to accomplish all of the above objectives by a commercially feasible and economical process.

These and other objects of the invention will become apparent from the following description and disclosure.

THE INVENTION

In accordance with this invention a liquid product mixture containing small amounts of an acidic platinum group metal catalyst is neutralized, clarified and decolorized by contacting said product with a basic anionic exchange resin having a free amino or quaternized ammonium salt functionality in an insoluble polymeric matrix.

The liquid product mixtures treated for catalyst removal are preferably organosilane or organosiloxane product mixtures containing up to 5,000 ppm acidic platinum group metal catalyst, most preferably a platinum or platinum/palladium catalyst. However, the present process can also be applied to liquid product mixtures resulting from the hydrogenation of fats and oils in the presence of an acidic platinum group metal catalyst or from platforming of gasoline and other products.

The insoluble polymeric matrix for the anionic exchange resin is suitably a cross-linked polymer as exemplified by styrene/divinylbenzene or acrylic copolymer matrices.

Generally, the resins of this invention have a macroreticular structure and are employed as discrete particles having a screen mesh size of 60 or more. The functionality of the basic anionic exchange resin is in the form of a lower alkyl tertiary amine or a quaternized ammonium salt containing ionized halide or preferably, ionized hydroxyl groups. Suitable quaternizing agents include lower alkyl halides, e.g. methyl chloride, dimethyl sulfate, benzyl halides, etc.

The ion exchange resins of this invention are produced from commercially available resins. The macroreticular ion exchange resins, as supplied by manufacturers, possess certain physical properties, namely a moisture content of 45–70%, an ion exchange capacity in excess of 0.5 meq/ml on a wet basis, a surface area greater than 20 m$^2$/g on dry basis and a particle size in the range of 20–50 mesh. Resins of this type which were tested, were found to have no positive effect in neutralizing and removing the soluble platinum catalyst. Therefore, it is critical to recondition these commercial ion exchange resins for use in the present process. The strongly or weakly basic anionic exchange resins of this invention are those having a moisture content of not more than 15% by weight, preferably not more than 10% by weight, an ion exchange capacity of from about 0.5 to about 40 meq/g on a dry basis and a particle size of between about 60 and about 1,000 mesh. Macroreticular ion exchange resins on a suitable matrix are commercially available as Amberlyst A-27, Amberlyst A-26, Amberlyst A-21, Amberlite IRA-938 and Amberlite IRP-276 supplied by Rohm and Haas Company and Dowex MSA-1, Dowex MWA-1, supplied by Dow Chemical Company, and others. In preparation for use in the present invention, the commercially available resins are either vacuum dried or washed with a lower alkanol, e.g. methanol or ethanol, dried at a temperature below decomposition to a moisture content within the above range and then ground to desired particle size.

The hydrosilylation reactions of the present invention include those wherein reactive silanic-hydrogen, i.e.

units of a silane or silicone compound or reactive hydrogen-siloxy, i.e.

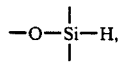

units of a polysiloxane polymer are added to an aliphatically unsaturated coreactant compound such as a substituted or unsubstituted alkene, substituted or unsubstituted alkene alkoxylates, unsaturated epoxides, and substituted or unsubstituted alkynes. The substituted groups are those which do not interfere with the addition reaction and include substituents such as $C_1$ to $C_{20}$ alkyl, halogen, cyano, hydroxy, alkoxy, alkyleneoxyalkyl, aryl, carboxy, amido, aldehyde, etc. Examples of such coreactants include ethylene, butene, tetradecene, hexadecene, octadecene, tributyldecene, diethyloctene, and halogenated derivatives thereof, styrene, halomethyl styrene, vinyl pyrrolidone, acrylonitrile, vinyl trimethyl silane, allyl chloride, allyl alcohol, methacrylic acid, acrylic acid, propargyl aldehyde, propargyl alcohol, 1-octyne, decynoic acid, polyacetylenes, ethoxylated or propoxylated derivatives of the above and other compounds which undergo hydrosilylation reaction to provide an organosilicone product containing a plurality of

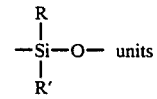

wherein R is a monovalent hydrocarbon group, such as lower alkyl or phenyl and R' is the corresponding saturated or partially saturated moiety generated by the addition of the ≡Si—H group across the unsaturated site of the unsaturated coreactant.

The hydrosilylation reactions are generally effected in the presence of a solvent such as benzene, toluene, xylene, dimethyl formamide and in the presence of a platinum group metal catalyst such as hexachloroplatinic acid, and others, defined by the formulae $H_2PtCl_6$, $H_2PtCl_4$, $NaHPtCl_6$, $NaHPtCl_4$, $KHPtCl_6$, $KHPtCl_4$, $Na_2PtCl_4$, $K_2PtCl_4$, the corresponding bromides and iodides of these platinum compounds as well as the palladium, rhodium, ruthenium and rhenium counterparts of the above platinum halide compounds and corresponding acids or mixtures of said catalysts such as for example a mixture of hexachloroplatinic acid and hexachloropalladinic acid. The reactants are diluted to between about 10% and about 100% with a suitable solvent while employing catalyst in a concentration of from about 15 to about 5,000 ppm with respect to total reactants.

The hydrosilylation reaction is generally carried out at a temperature between about 25° C. and about 160° C., preferably between about 80° C. and about 120° C. under a pressure of from about 0 psig to about 50 psig for a period of from about 1 hour to several days, during which silanic-hydrogen or hydrogen-siloxy units of the silicone polymer are added across the C to C sites of unsaturation of the alkene or alkyne compound in the presence of a small amount of acidic platinum catalyst, e.g. between about 15 ppm and about 5,000 ppm, more often between about 20 and about 200 ppm, which is entrained in the polymeric organosilicone product.

In accordance with the present invention the resulting product mixture is then neutralized and clarified by contacting with the basic anionic exchange resin herein defined. The clarification step can be carried out by adding between about 0.1 and about 10% by weight of resin based on the total product and the amount of catalyst in solution to be removed. Usually the addition of between about 0.7% and about 5%, of the basic anionic exchange resin is sufficient to provide adequate catalyst removal. The product mixture to which the anion exchange resin is added for catalyst removal can be any of the hydrosilylation reaction mixtures described above or can be a commercially available organosilicone product which has objectionable haze or color due to entrainment of from about 1 ppm or more platinum catalyst. The commercial product is dissolved in a suitable solvent and treated in accordance with this invention. Also, the product mixture can be the crude liquid product of a reaction effected in the presence of one or more of the aforedescribed catalysts, such as the crude product mixture obtained from platforming reactions, the hydrogenation of fats and oils, hydrogenation reactions, hydroforming reactions, oxidation of higher alcohols, ring opening polymerization reactions, and others which contain up to 5,000 ppm of one or more of the aforedescribed platinum group metal catalysts. The resulting mixture is agitated over a period of from about 1 to about 24 hours, as in a batch operation. Alternatively, the neutralization and clarification step can be carried out in a continuous manner by passing the reaction mixture through one or more fixed beds of the basic anionic exchange resin until a clear, colorless product is withdrawn. Such continuous operation may involve several ion exchange beds. The critical size of the anion exchange resin may vary within the range of from about 60 to about 1,000 mesh, preferably from about 100 to about 325 mesh size, based on dry resin.

During contact with the ion exchange resin, the platinum catalyst entrained in the product is effectively removed by bonding to the resin. The clarification step is effected within the range of the synthesis operating parameters, preferably at a temperature of between about 25° and about 120° C., most preferably between about 40° and about 95° C.

The rate of acidic catalyst neutralization and extraction with ion exchange resin increases with contact time, temperature the amount of solvent and the type and particle size of the resin, as well as with the amount of anionic exchange resin employed.

In a batch operation, after clarification and decolorization are complete, the reaction mixture is filtered and the filtrate collected as a clear colorless solution containing product and solvent which can be separated by conventional means, such as distillation. The filtration step can be carried out in the presence of a combustible cellulosic filter aid, such as for example Solka-Floc SW 40.

In a continuous operation, as in one or more contacting columns, the reaction mixture is passed through the resin containing column or columns until clarification and decolorization are complete. The filter cake then can be treated for platinum recovery. Platinum recovery can be accomplished by leaching the resin with an inorganic hydroxide solution, such as sodium hydroxide, potassium hydroxide, ammonium hydroxide, employed in a concentration of between about 1% and about 15%, preferably between about 4% and about 10%, to leach and convert the strongly held platinum group metal anions to a soluble salt. The acid platinum type catalyst can be regenerated by contacting the salt solution with a cationic exchange resin, e.g. AMBERLYST 15, whereby a chloroplatinic acid is reformed. Both anionic and cationic exchange resins can be economically and efficiently regenerated for reuse.

Alternatively, the filter cake from a batch operation or the bed of ion exchange resin from a continuous operation, together with any combustible filter aid material which may have been employed, can be incinerated, whereupon the metallic platinum group metal is recovered as elemental metal. For example, one such recovery operation involves heating the residue in a starve air furnace where, in the presence of heat and a slow flow of air, the combustible material is ignited and carbon oxides are liberated and removed. Incineration of the ion exchange resin is generally carried out at a temperature of between about 315° C. and about 430° C. and trace amounts of the platinum group metal contained therein can be recovered in yields as high as 99.5% in 99.95% purity. The platinum group metal can then be regenerated to the desired acid catalyst by conventional methods or the elemental metal can be used as such in various processes, such as in electroplating or other uses as in dentistry, jewelry and material for laboratory equipment.

It will become obvious that the present treatment with the ion exchange resins of this invention can be incorporated as a standard step in the syntheses of organosilane or organosilicone compounds or it can be employed to treat commercially available organosilicone products which retain a hazy or yellowish tint due to entrainment of platinum catalyst.

Having thus generally described the invention, reference is now had to the following examples which illustrate embodiments of the invention but are not to be construed as limiting to the scope thereof as more broadly set forth above and in the appended claims.

EXAMPLE 1

All of the ion exchange resins used in the following examples derived from commercially available ion exchange resins are reconditioned before use to the desired water content and particle size according to the following methods:

1. Removal of water from the resin:
The removal of water is effectively carried out by either of the following two methods.

A  The resin is vacuum-dried to the desired water content most preferably to less than 5%, at reduced pressure and at a temperature below the decomposition temperature of the functional groups.

B  A column charged with the resin is treated with a volume of lower alkyl hydroxide, i.e. methanol, equal to four times the volume of the bed of resin in the column, allowing the methanol to flow downward through the bed within a period of about one hour. An alcohol-free resin is then obtained by removing the residual methanol under atmospheric or reduced pressure at room temperature.

2. Particle size reduction of resin.
After the resin is dried to the desired water content, it is subjected to crushing in a hammer mill (micropulverizor), to a particle size of 60 to 1,000 mesh, preferably between 100–325 mesh.

EXAMPLE 2

To a 2-liter, three-necked round bottom flask, equipped with a mechanical stirrer, water condenser, thermometer and nitrogen sparge, was added 1250 g of a solution composed of 1,000 g of a crude unneutralized organosilicone, ALKASIL NEP 73-70* and 250 g of xylene. To this was added 10 g of 160 mesh granular, weakly basic anionic exchange resin** having a moisture content of less than 5%; an anionic exchange capacity of 1.25 meq/ml and a free —N(CH$_3$)$_2$ functionality bonded to a styrene-divinyl benzene matrix. The mixture was heated to 90° C. and maintained under agitation for 16 hours. The mixture was then rapidly filtered and allowed to cool to room temperature after which it was analyzed for platinum content, coloration and haze. The treated product was compared with untreated ALKASIL NEP 73-70. The results of the comparison are as reported in Table I.

* a dimethyl polysiloxane glycol copolymer, supplied by Alkaril Chemicals Limited
** derived from Amberlyst A-21

TABLE I

| ALKASIL NEP 73-70 | | |
|---|---|---|
| Pt content (ppm) | | |
| untreated | 77.40 | |
| treated | 0.39 | 99.5% Recovery |

TABLE I-continued

| ALKASIL NEP 73-70 | |
|---|---|
| Color Value (Gardner Scale) | |
| untreated | 4 |
| treated | <1 |
| Appearance | |
| untreated | hazy, dark amber |
| treated | clear, colorless |

EXAMPLE 3

Example 2 was repeated except that ALKASIL NO 1223-12*, supplied by ALKARIL CHEMICALS LIMITED, was substituted for ALKASIL NEP 73-70. Also, 15 g of the anion exchange resin were employed and the mixture was heated to 100° C. for 16 hours. The results of this treatment are reported in following Table II.

TABLE II

| ALKASIL NO 1223-12 | | |
|---|---|---|
| Pt content (ppm) | | |
| untreated | 30.90 | |
| treated | 0.47 | 98.5% Pt recovery |
| Color Value (Gardner Scale) | | |
| untreated | 3 | |
| treated | <1 | |
| Appearance | | |
| untreated | hazy, amber | |
| treated | clear, colorless | |

EXAMPLE 4

Example 2 was repeated except that GE SF-1188** was substituted for ALKASIL NEP 73-70 and the mixture was heated to 70° C. for 12 hours. The results of this treatment are reported in following Table III.
* an epoxy modified dimethyl polysiloxane
** a dimethylpolysiloxane glycol copolymer, supplied by General Electric Company

TABLE III

| GE SF 1188 | | |
|---|---|---|
| Pt content (ppm) | | |
| untreated | 15.30 | |
| treated | 0.24 | 98.4% Pt recovery |
| Color value (Gardner Scale) | | |
| untreated | 1.5 | |
| treated | <1 | |
| Appearance | | |
| untreated | hazy, amber | |
| treated | clear, colorless | |

EXAMPLE 5

Example 2 was repeated except that DC-190* was substituted for ALKASIL NEP 73-70 and 20 g of the anion exchange resin was used in place of 10 g. The mixture was heated to 85° C. for 34 hours. The results of this treatment are reported in Table IV.
* a dimethylpolysiloxane glycol, acetoxy capped copolymer supplied by Dow Corning Corp.

TABLE IV

| DC-190 | | |
|---|---|---|
| Pt. content (ppm) | | |
| untreated | 8.22 | |
| treated | <0.30 | 96.4% Pt recovery |
| Color value (Gardner Scale) | | |
| untreated | 1 | |
| treated | <1 | |
| Appearance | | |
| untreated | hazy, light amber | |
| treated | clear, colorless | |

EXAMPLE 6

Example 5 was repeated except that Tegostab B-8408* was substituted for ALKASIL NEP 73-70 and the mixture was heated to 87° C. for 31 hours. The results of this treatment are reported in following Table V.

TABLE V

| Tegostab B-8408 | | |
|---|---|---|
| Pt. content (ppm) | | |
| untreated | 15.40 | |
| treated | <0.30 | 98.1% Pt recovery |
| Color value (Gardner Scale) | | |
| untreated | 2 | |
| treated | 1 | |
| Appearance | | |
| untreated | hazy, yellow | |
| treated | clear, slight yellow cast | |

Goldschmidt Co.

TABLE V

| Tegostab B-8408 | | |
|---|---|---|
| Pt. content (ppm) | | |
| untreated | 15.40 | |
| treated | <0.30 | 98.1% Pt recovery |
| Color value (Gardner Scale) | | |
| untreated | 2 | |
| treated | 1 | |
| Appearance | | |
| untreated | hazy, yellow | |
| treated | clear, slight yellow cast | |

EXAMPLE 7

Example 2 was repeated except that Tegostab B-8407* was substituted for ALKASIL NEP 73-70 and the mixture was heated to 86° C. for 8.5 hours. The results of this treatment are reported in following Table VI.
* a dimethylpolysiloxane glycol copolymer supplied by Goldschmidt Co.

TABLE VI

| Tegostab B-8407 | | |
|---|---|---|
| Pt. content (ppm) | | |
| untreated | 34.1 | |
| treated | <0.3 | at least 99.1% Pt. recovery |
| Color value (Gardner Scale) | | |
| untreated | 4 | |
| treated | 1 | |
| Appearance | | |
| untreated | hazy, brown | |
| treated | clear, slight yellow cast | |

EXAMPLE 8

Example 2 was repeated except that Silwet L-7600* was substituted for ALKASIL NEP 73-70 and the mixture was heated to 80° C. for 6 hours. The results of this treatment are reported in following Table VII.

* a dimethylpolysiloxane glycol, methoxy capped copolymer, supplied by Union Carbide Corp.

TABLE VII

| Silwet L-7600 | | |
|---|---|---|
| Pt. content (ppm) | | |
| untreated | 7.25 | |
| treated | <0.10 | at least 98.6% Pt. recovery |
| Color value (APHA) | | |
| untreated | 500 | |
| treated | 100 | |
| Appearance | | |
| untreated | clear, slight yellow | |
| treated | clear, colorless | |

EXAMPLE 9

Example 2 was repeated except that Ucarsil T-29* was substituted for ALKASIL NEP 73-70 and the mixture was heated to 76° C. for 6 hours. The results of this treatment are reported in following Table VIII.

* an epoxy modified dimethyl polysiloxane, supplied by Union Carbide Corp.

TABLE VIII

| Ucarsil T-29 | | |
|---|---|---|
| Pt. content (ppm) | | |
| untreated | 1.49 | |
| treated | <0.30 | at least 79.9% Pt. recovery |
| Color value (APHA) | | |
| untreated | 150 | |
| treated | 10 | |
| Appearance | | |
| untreated | clear, slight yellow | |
| treated | clear, colorless | |

COMPARATIVE EXAMPLE 10

To a 2-liter, three-necked round bottom flask equipped with a mechanical stirrer, water condenser, thermometer and nitrogen sparge, was added 1500 g of a solution composed of 1,000 g of ALKASIL NE 58-50* and 500 g of xylene. To this was added 10 g of a predried (less than 5% moisture), macroreticular, strongly basic anion exchange resin, Amberlyst A-27, having a particle size in the range of 25 to 50 mesh, a surface area of 65 m²/g, anion exchange capacity of 0.7 meq/ml and a quaternary ammonium salt functionality in the hydroxide form bonded to a styrene-divinyl benzene matrix. The mixture was agitated at room temperature for 144 hours, during which time, the color of the reaction mixture was monitored by filtering small samples at different times. The treated product was compared with untreated ALKASIL NE 58-50. The results of the comparison are as reported in Table IX.

* a dimethylpolysiloxane glycol copolymer, supplied by Alkaril Chemicals Limited

TABLE IX

| ALKASIL NE 58-50 | | |
|---|---|---|
| Pt. content (ppm) | | |
| untreated | 96.97 | 0% Pt. recovery |
| treated | 96.97 | |
| Color value (Gardner Scale) | | |

TABLE IX-continued

| ALKASIL NE 58-50 | | |
|---|---|---|
| untreated | 2 | |
| treated | 2 | |
| Appearance | | |
| untreated | hazy, amber | |
| treated | hazy, amber | |

EXAMPLE 11

Example 10 was repeated except that ALKASIL NEP 73-70 was substituted for ALKASIL NE 58-50 and the strongly basic anion exchange resin, Amberlyst A-27, reconditioned to a moisture content of <5% and a particle size in the range of 170 to 325 mesh. The mixture was agitated at room temperature for 20 hours. The results of this treatment are reported in following Table X.

TABLE X

| ALKASIL NEP 73-70 | | |
|---|---|---|
| Pt. content (ppm) | | |
| untreated | 195.7 | |
| treated | <0.3 | 99.85% Pt. recovery |
| Color value (Gardner Scale) | | |
| untreated | 4.5 | |
| treated | <1 | (1 after 4 hours mixing) |
| Appearance | | |
| untreated | hazy, amber | |
| treated | clear, colorless | (cleared after 4 hours mixing) |

EXAMPLE 12

To a flask equipped with mechanical stirrer, thermometer and nitrogen sparge, was added 240 g of a solution composed of 200 g of ALKASIL NE 58-50 and 40 g of xylene. To this was added 2.70 g of reconditioned strongly basic anion exchange resin, Amberlite IRA-938, having a moisture content of <5%, particle size in the range of 170 to 325 mesh and a quaternary ammonium salt functionality in the hydroxide form bonded to a styrene-divinylbenzene matrix. The mixture was agitated at room temperature for 105.5 hours and then filtered. The treated product was compared with untreated ALKASIL NE 58-50. The results of the comparison are as reported in Table XI.

TABLE XI

| ALKASIL NE 58-50 | | |
|---|---|---|
| Pt. content (ppm) | | |
| untreated | 207.83 | |
| treated | 3.00 | 98.6% Pt. recovery |
| Color value (Gardner Scale) | | |
| untreated | 5 | |
| treated | 1 | |
| Appearance | | |
| untreated | hazy, amber | |
| treated | clear, slight amber cast | |

COMPARATIVE EXAMPLE 13

To a flask, equipped with a magnetic bar, thermometer and nitrogen sparge, was added 150 g of a solution composed of 100 g of ALKASIL NEP 73-70 and 50 g of xylene. To this was added 0.036 g of acrylic based polymeric amine-borane reductive resin, Amborane 345, having water content of less than 2% and particle size in the range of 30-60 mesh. The mixture was agitated at room temperature for five days and then filtered. The treated product was compared with untreated ALKASIL NEP 73-70. The results of the comparison are as reported in Table XII.

TABLE XII

| ALKASIL NEP 73-70 | | |
| --- | --- | --- |
| Pt. content (ppm) | | |
| untreated | 206.89 | |
| treated | 206.89 | 0% Pt. recovery |
| Color value (Gardner Scale) | | |
| untreated | 4 | |
| treated | 4 | |
| Appearance | | |
| untreated | hazy, amber | |
| treated | hazy, amber | |

COMPARATIVE EXAMPLE 14

Example 2 was repeated except that macroreticular weakly basic Amberlyst A-21 having a —N(CH$_3$)$_2$ functionality and a particle size of 20 to 50 mesh, was dried to a water content of less than 5%. The mixture was heated to 85° C. and maintained under agitation for 5 days. The results of this treatment are reported in following Table XIII.

TABLE XIII

| ALKASIL NEP 73-70 | | |
| --- | --- | --- |
| Pt. content (ppm) | | |
| untreated | 77.40 | 0% Pt. recovery |
| treated | 77.40 | |
| Color value (Gardner Scale) | | |
| untreated | 4 | |
| treated | 4 | |
| Appearance | | |
| untreated | hazy, amber | |
| treated | hazy, amber | |

EXAMPLE 15

To a 2-liter, four-necked round bottom flask equipped with a mechanical stirrer, thermometer, water condenser and nitrogen sparge was added 344.5 g (0.596 mole) of hydropolysiloxane fluid (MW 578) and 250 g of xylene. The two components were then heated to 85° C. with constant stirring and 150 ppm of hexachloroplatinic acid solution was added to the reaction flask. To the reaction flask was also added dropwise 655.5 g (1.311 mole) of alkoxylated allyl alcohol initiated polyether. The reaction exothermed to 115° C. and after cooling to 100° C., the mixture was kept at that temperature for 8 hours under atmospheric pressure.

After the reaction was complete, the reaction mixture was cooled to 80°-90° C. and 10 g of the anionic exchange resin of Example 1 was added and agitated for 20 hours at the above temperature, after which the reaction mixture was filtered and xylene distilled off at reduced pressure to provide 1,000 g of a clear, colorless product.

The residue of anion exchange resin containing bonded hexachloroplatinate ions is washed three times with 35 ml portions of 4% sodium hydroxide solution over a period of 5 hours at 25° C. to leach out the hexachloroplatinate ions from the resin and to convert them to the corresponding disodium hexachloroplatinate (IV) salt.

The disodium hexachloroplatinate salt solution can be regenerated to hexachloroplatinic acid by contact with an acidic cationic exchange resin, such as Amberlyst 15 or Dowex MSC-1. The anionic and cationic resins can be regenerated by treatment with an alkali wash and by treatment with hydrochloric acid solution, respectively.

The foregoing examples serve to illustrate the substantially complete removal of acidic platinum group metal catalysts from liquid product mixtures when employing the anionic exchange resins of this invention. It will be understood that any of the other liquid product mixtures herein described and that liquid product mixtures containing any of the other dissolved platinum group metal acid catalysts described int the foregoing disclosure, such as the Pd, Rh, Ru, acid halide catalysts can be substituted in Examples 2-9, 11, 12 and 15 to effect the substantially complete removal of catalyst from the liquid product mixtures; and also that, by substitution of these other catalyst compounds, after reacting with the present anionic exchange resins, the catalyst can be regenerated in high yield and purity in accordance with the method outlined in Example 15.

What is claimed is:

1. The process for removing a platinum group metal compound from a liquid product mixture containing from about 1 to about 5,000 ppm of an acidic platinum group metal compound which comprises (a) contacting and agitating said liquid with basic macroreticular anionic exchange resin particles having a particle size of from about 60 to about 1,000 mesh, a moisture content less than 15% and an ion exchange capacity of from about 0.5 to about 40 meq/ml for a period and at a temperature sufficient to react said acidic platinum metal group compound with said ion exchange resin and (b) separating a clear colorless liquid product from said reacted ion exchange resin particles.

2. The process of claim 1 wherein said liquid product mixture is an organosilicone or organosilane product solution derived from the reaction of a hydropolysiloxane or an organosilane in the presence of an acidic platinum group metal catalyst.

3. The process of claim 2 wherein said catalyst is a catalyst containing acidic platinum.

4. The process of claim 3 wherein said catalyst is hexachloroplatinic acid and said liquid product contains between about 15 and about 200 ppm hexachloroplatinic acid.

5. The process of claim 1 wherein the liquid product mixture is contacted with the ion exchange resin for a period of from 1 to 24 hours at a temperature of between about 25° and 120° C.

6. The process of claim 1 wherein the separated anionic exchange resin particles containing the acidic platinum group metal ions are treated with an aqueous inorganic hydroxide solution to extract and to convert said acidic platinum group metal ions to a recoverable salt.

7. The process of claim 1 wherein said anionic exchange resin have a moisture content less than 10% and a particle size of between about 100 and about 325 mesh on an insoluble cross-linked polymeric matrix.

8. The process of claim 1 wherein said anionic exchange resin containing platinum group metal ions is separated from the liquid product mixture by filtration.

9. The process of claim 1 wherein said contacting of liquid product mixture and said anionic exchange resin is effected over a period of from 1 to 24 hours with between about 0.1 weight % and about 10 weight % of anionic exchange resin based on total liquid product mixture.

10. The process of claim 9 wherein the amount of anionic exchange resin is between about 0.7 weight % and about 5 weight %.

11. The process of claim 1 wherein said contacting of liquid product mixture and said anionic exchange resin is effected at a temperature of between about 40° C. and about 95° C.

12. The process of claim 1 wherein said reacted anionic exchange resin particles containing platinum group metal ions, after separation of liquid product, are contacted with a basic aqueous solution of an alkali or alkaline earth metal hydroxide for a period and at a temperature sufficient to extract and to convert said platinum group metal ions to a soluble metal salt and recovering said salt from said ion-exchange resin particles.

13. The process of claim 12 wherein said platinum group metal salt is a di-alkali metal hexachloroplatinate salt and said di-alkali metal hexachloroplatinate salt solution is separated from said anionic exchange resin by contact with a cationic exchange resin to convert said salt to hexachloroplatinic acid.

14. The process of claim 12 wherein the basic aqueous solution is a metal hydroxide solution of from about 1 to about 15% metal hydroxide concentration and the mole ratio of metal hydroxide to platinum group metal ion is between about 2:1 and about 10:1.

15. The process of claim 1 wherein said reacted anionic exchange resin particles containing bound platinum group metal ions, after separation of said liquid product, are incinerated to recover platinum group metal in the elemental state.

16. The process of claim 15 wherein said anionic exchange resin containing bound platinum group metal ions are incinerated at a temperature between about 315° C. and about 430° C.

17. The process of claim 16 wherein the bound platinum group metal ions are hexachloroplatinate ions and incineration of said resin generates elemental platinum.

* * * * *